(12) United States Patent
Foulkes

(10) Patent No.: US 7,175,594 B2
(45) Date of Patent: Feb. 13, 2007

(54) OPHTHALMIC SULCUS SPECULUM

(76) Inventor: Richard B. Foulkes, FutureVision, Laser and Research Center, 40 S. Clay, Suite 9W, Hinsdale, IL (US) 60521

( * ) Notice: Subject to any disclaimer, the term of this patent is extended or adjusted under 35 U.S.C. 154(b) by 0 days.

(21) Appl. No.: 10/349,061

(22) Filed: Jan. 21, 2003

(65) Prior Publication Data

US 2003/0171656 A1    Sep. 11, 2003

Related U.S. Application Data

(60) Provisional application No. 60/351,219, filed on Jan. 22, 2002.

(51) Int. Cl.
*A61B 1/32*    (2006.01)
*A61F 9/00*    (2006.01)

(52) U.S. Cl. .............. 600/236; 600/219; 600/225
(58) Field of Classification Search .......... 600/236, 600/235, 231, 227, 225, 219, 232; 606/107
See application file for complete search history.

(56) References Cited

U.S. PATENT DOCUMENTS

| | | | |
|---|---|---|---|
| 1,853,238 A | 4/1932 | Shields | |
| 2,171,070 A | 8/1939 | Raible | 20/68 |
| 2,294,186 A | 8/1942 | Kirschbaum | 128/269 |
| 3,165,773 A | 1/1965 | Palpacelli | 15/310 |
| 3,179,108 A | 4/1965 | Bloch et al. | 128/269 |
| 3,199,512 A * | 8/1965 | Cavanaugh et al. | 604/106 |
| 3,286,693 A | 11/1966 | Clarke, Jr., et al. | 119/102 |
| 3,307,818 A | 3/1967 | Cocito | 248/362 |
| 3,324,855 A | 6/1967 | Heimlich | 128/269 |
| 3,394,702 A | 7/1968 | Heimlich et al. | 128/269 |
| 3,520,300 A * | 7/1970 | Flower, Jr. | 604/269 |
| 3,608,946 A | 9/1971 | Erickson et al. | 294/64 |
| 3,783,863 A | 1/1974 | Kliever | 128/134 |
| 4,321,916 A | 3/1982 | McKee | 128/20 |
| 4,494,254 A | 1/1985 | Lopez | 3/13 |
| 4,525,166 A | 6/1985 | Leclerc | 604/133 |
| 4,533,352 A | 8/1985 | Van Beek et al. | 604/317 |
| 4,652,255 A | 3/1987 | Martinez | 604/27 |
| 4,671,790 A | 6/1987 | Nishi | 604/131 |
| 4,790,833 A | 12/1988 | Schmidt | 604/317 |

(Continued)

OTHER PUBLICATIONS

EyeWorld, p. 17-22 (Jun. 2002).

(Continued)

*Primary Examiner*—Pedro Philogene
(74) *Attorney, Agent, or Firm*—John H. Thomas, P.C.

(57) ABSTRACT

Devices in accordance with certain embodiments of the present sulcus speculum are designed to be placed into the sulcus of an eye to perform one or more of the following functions: evacuation of fluid, opening of the lids, and application of drugs such as anesthetic or antibiotics. The present devices can include a sponge positioned around (a) an aspiration tube for withdrawing fluid and (b) an arm of a speculum. Other variations of the present devices include those with an aspiration tube for withdrawing fluid, the tube being positioned in a trough defined by an arm of a speculum. Alternatively, the speculum arm can define a passage for holding the aspiration tube. In that alternate embodiment, the portion of the speculum arm defining the passage has openings for passing fluid into the passage so that the aspiration tube in the passage can then remove fluid.

7 Claims, 6 Drawing Sheets

U.S. PATENT DOCUMENTS

| | | | |
|---|---|---|---|
| 4,905,711 A | 3/1990 | Bennett et al. | 128/869 |
| 4,906,261 A | 3/1990 | Mohajer | 96/225 |
| 5,034,006 A | 7/1991 | Hosoda et al. | 604/317 |
| 5,123,902 A | 6/1992 | Muller et al. | 604/21 |
| 5,171,254 A * | 12/1992 | Sher | 606/166 |
| 5,209,747 A | 5/1993 | Knoepfler | 606/16 |
| 5,217,460 A | 6/1993 | Knoepfler | 606/52 |
| 5,300,087 A | 4/1994 | Knoepfler | 606/207 |
| 5,372,587 A | 12/1994 | Hammerslag et al. | 604/95 |
| 5,378,234 A | 1/1995 | Hammerslag et al. | 604/95 |
| 5,437,651 A | 8/1995 | Todd et al. | 604/313 |
| 5,618,261 A * | 4/1997 | Nevyas | 600/236 |
| 5,628,735 A * | 5/1997 | Skow | 604/317 |
| 5,674,226 A | 10/1997 | Doherty et al. | 606/107 |
| 5,755,700 A | 5/1998 | Kritzinger et al. | 604/257 |
| 5,860,985 A * | 1/1999 | Anschutz | 606/107 |
| 5,893,863 A | 4/1999 | Yoon | 606/170 |
| 5,897,507 A | 4/1999 | Kortenbach et al. | 600/562 |
| 5,919,202 A | 7/1999 | Yoon | 606/170 |
| 5,941,873 A | 8/1999 | Korenfeld | 606/1 |
| 5,971,977 A * | 10/1999 | Korenfeld | 606/1 |
| 5,984,913 A | 11/1999 | Kritzinger et al. | 604/541 |
| 6,063,021 A | 5/2000 | Hossain et al. | 600/37 |
| 6,142,956 A | 11/2000 | Kortenbach et al. | 600/564 |
| 6,174,292 B1 | 1/2001 | Kortenbach et al. | 600/565 |
| 6,267,752 B1 | 7/2001 | Svetliza | 604/294 |
| 6,283,913 B1 * | 9/2001 | Seibel | 600/236 |
| 6,290,685 B1 | 9/2001 | Insley et al. | 604/317 |

OTHER PUBLICATIONS

"Ophthalmic Titanium Surgical Instruments, New Dimensions", Duckworth & Kent, 2001.

* cited by examiner

OPHTHALMIC SULCUS SPECULUM

CROSS-REFERENCE TO RELATED APPLICATION(S)

This application is related to and claims priority benefits from U.S. Provisional Patent Application Ser. No. 60/351,219 filed Jan. 22, 2002. The '219 provisional application is hereby incorporated by reference herein in its entirety.

FIELD OF THE INVENTION

Aspects of the present invention are directed to the field of ophthalmic devices. More particularly, aspects of the present invention are directed to speculums for placement adjacent the sulcus, which is the region under the eyelid where the covering of the lid and globe fold back on themselves, during ophthalmic procedures.

BACKGROUND OF THE INVENTION

A class of instruments known as speculums facilitates access to the eye during ophthalmic procedures by spreading the lids. Speculums are of many designs but lid speculums work by using a wire or blade to wrap around the eyelid margin several millimeters near the midpoint to spread the eyelids gaining exposure of the ocular surfaces.

Problems with conventional speculums occur when the lid length is short, limiting the distance that the lids can be retracted, or when the eye is deep-set. These two problems lead to a "squaring" of the view and limit the working area and visibility. Additionally the lids tend to rise up when stretched tight, creating a potential space for fluid to pool. Pooling of fluid limits visibility of the surgeon further and allows for bacteria and eye secretions to potentially enter the eye, especially in cataract surgery where a large amount of water is used in the extraction of the lens. Elderly eyes become recessed from the loosening of the fat pads, which further complicates the view with water filling into the space formed by the recession. Cataract surgery is the most common ophthalmic procedure with over a million procedures performed each year.

A tube connected to a suction source at one end and having an opening at the other end can be used to suction water from the surgical site. Such a suction tube is rarely used in ophthalmic procedures as it represents an additional source of obstruction to view and free movement.

Another method to solve the problem of pooling includes a wick of sponge that works slowly by osmosis to provide a drain out of the side of the lid. This passive method is reasonably effective in removing small amounts of fluid but fails in deep-set eyes and the wick often floats out of the eye. Positioning the patient's head to be angled to the side can be helpful but often limits the microscopic view into the eye from obstruction by the nose or brow.

Some lid speculums for opening eyelids have hollow tubing with openings or holes formed therein, the tubing being attached to suction for removal of water or fluids from the orbital/ocular area. These lid speculums can perform aspiration, however, the aspiration is often ineffective because the holes in these speculums are adjacent the lid margin which is often well above the corneal surface, making the holes incapable of removing the water. The poor visibility encountered by the surgeon while operating on a patient increases the risk of a poor surgical outcome. Viewing the eye under water affects the surgeon's view into the eye altering depth perception and magnification. The risk of infection from this water getting into the eye is also increased.

Recently, a popular procedure using ultraviolet laser to reshape the cornea to change the refractive power of the eye was developed. In this procedure the front surface of the cornea is exposed to 193-nanometer (nm) light to remove a precise amount of tissue to change the curvature of the anterior cornea. In a small eye, the problem of fluid clearance is made worse by the tendency of the inner part of the cornea (stroma) to absorb water when the stroma is exposed. Tear film or water from the device (known as a microkeratome and used to open the anterior cornea) quickly absorbs into the inner tissue of the cornea. The water slows the absorption of the 193 nm laser and alters the treatment shape leading to problems with the patient's vision correction including aberrational vision. Currently, wicking methods and aspirating speculums are used but are often inadequate due to the raising of the ports of conventional aspirating speculums above the ocular surface. Wicking dams can be helpful but are often overwhelmed by the tear film. By the time wicking dams are in place the fluid is often already on and in the stromal bed. Manual removal of fluid by employing a sponge necessitates stopping the surgical procedure, which changes the hydration and dehydration of the cornea and reduces the precise standardization required to attain good surgical results for the patient.

Many ophthalmic procedures are performed using topical anesthetic. These drugs are applied as topical drops and are ideally applied under the lids to reach the sulcus, the sulcus being the point under the lid where the covering of the lid and globe fold back on themselves. A sponge can be soaked with anesthetic and placed under the lid to keep the drug from diffusing away in the tear film. These drugs are somewhat toxic to the anterior corneal surface and especially in refractive surgery many surgeons try to avoid drug exposure to the front surface by using a soaked sponge. The topical drugs are fairly short acting, so to add more drugs by conventional topical methods required using a sponge and stopping surgery temporarily to apply additional drugs. Other techniques involve drugs that are injected under the conjunctiva, called peribulbar. The peribulbar techniques largely work by continuous leakage of the drugs out of the wound created. To avoid this peribulbar injection technique, a continuous drug delivery system is desirable. Thus, there is a desire to find another device for applying topical drugs during ophthalmic procedures.

In certain emergency situations, like acid or alkali exposure to the eye, where continuous flushing of the eye is used to normalize the PH, no current device exists to secure a flow system into the eye. Furthermore, in certain infectious emergencies it would be advantageous to have a comfortable system to allow for continuous infusion of antibiotic or other drugs onto the ocular surfaces.

In refractive surgery called Lasik, a device known as a microkeratome is used on the front surface of the eye to create a thin slice of tissue. This thin slice of tissue is folded back and the exposed inner surface of the cornea is lasered. The microkeratome is a mechanized device with an oscillating blade that is driven across the eye either manually or with a motor drive. The device is held on the eye by a vacuum ring that pulls the cornea up into the ring to come into contact with the blade. If the microkeratome contacts an obstruction during the pass it slows down or is deflected up. The result of slowing down or stopping is a wave on the surface to be lasered that can cause irregular vision. If the obstruction is hard enough, the ring can be dislodged and a partial flap is created usually leading to an aborted procedure. The most common cause of an obstruction is the microkeratome bumping into a lid speculum, especially in a tight eye. Thus a device to hold the lid open, without obstructing the microkeratome, would be particularly advantageous.

The lowest point in the eye when the patient is laying flat is the sulcus or the point where the clear covering of the eye folds back on itself around the globe. Conventional fluid removal systems do not adequately reach the sulcus because such systems are attached to the lid margin and tend to rise away from the sulcus when lids are spread open, especially when such systems are attached to a small lid.

SUMMARY OF THE INVENTION

Some embodiments of the present sulcus speculum address some of the above problems by placing an instrument into the sulcus for one or more of the following: evacuation of fluid, opening of the lids, and application of drugs such as anesthetic or antibiotic. In one embodiment, a device for placement adjacent a sulcus during ophthalmic surgery includes a speculum having an arm, an aspiration tube having at least one opening formed therein, and a porous member. The porous member receives at least a portion of the aspiration tube and at least a portion of the speculum arm.

In another embodiment, a device for placement adjacent a sulcus during ophthalmic surgery includes a speculum having an arm, wherein a portion of the arm defines a trough, and an aspiration tube having at least one opening formed therein. At least a portion of the aspiration tube is disposed in the trough.

In a further embodiment, a device for placement adjacent a sulcus during ophthalmic surgery includes a speculum having at least one arm having a portion defining a passage and an aspiration tube having at least one opening formed therein. At least a portion of the aspiration tube is disposed in the passage.

A further aspect of the present sulcus speculum is a device for placement adjacent a sulcus during ophthalmic surgery including a speculum having an arm with curvature adapted to reach the sulcus associated with an eyelid, wherein the arm has a opening formed therein.

DETAILED DESCRIPTION OF PREFERRED EMBODIMENT(S)

Figure 1:
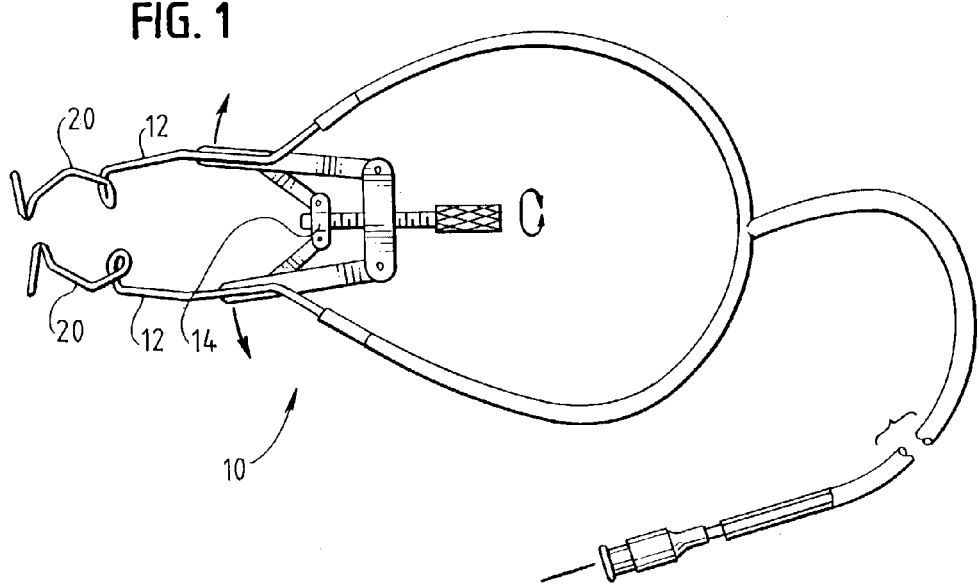
FIG. 1 depicts a conventional wire speculum.
Figure 2:
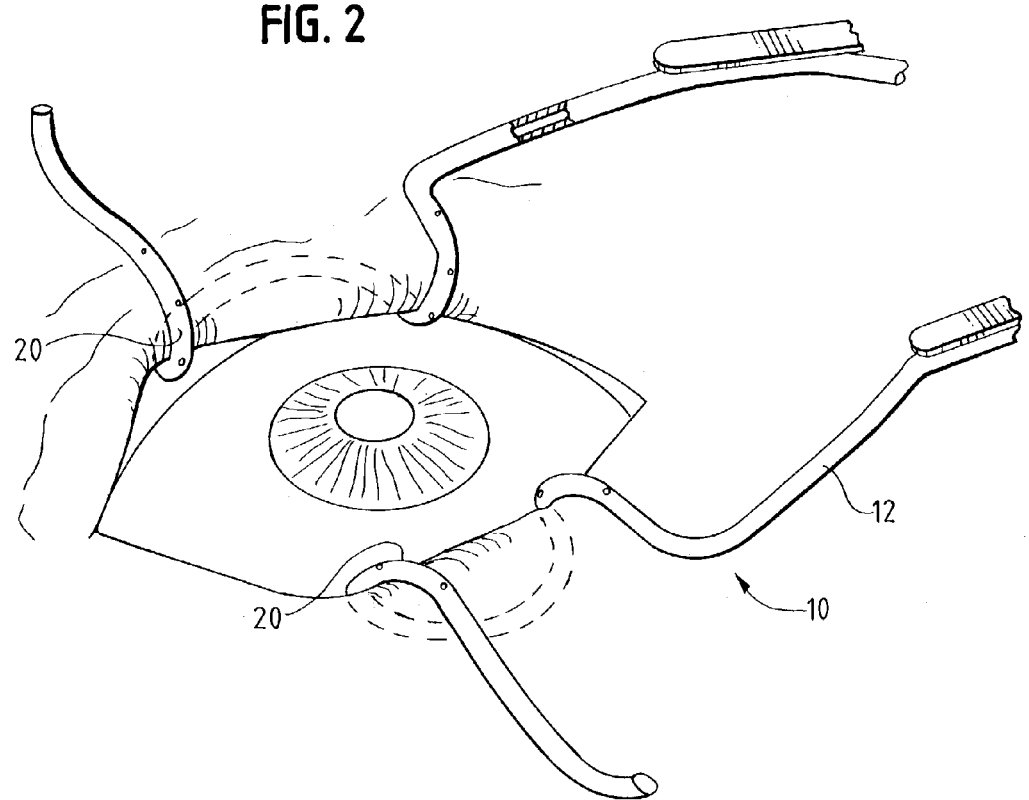
FIG. 2 depicts a portion of a conventional wire speculum, such as that illustrated in FIG. 1, having loops to engage eyelid margins.

FIGS. 1 and 2 depict a conventional wire speculum 10, which is used to access the eye during ophthalmic procedures by spreading the lids. The speculums depicted in FIGS. 1 and 2 employ a wire or blade to wrap around the eyelid margin several millimeters near the midpoint to spread the eyelids, thereby exposing the ocular surface.

Figure 3:
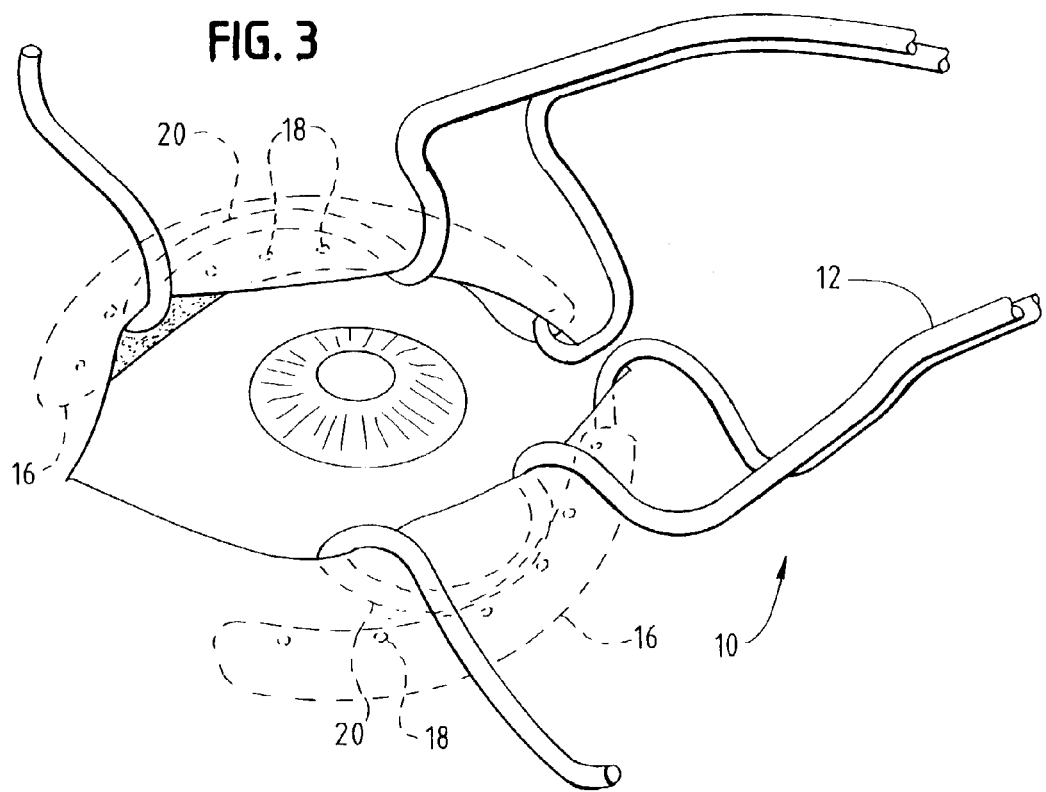
FIG. 3 depicts a portion of a wire speculum having loops to engage lid margins and a portion of one embodiment of the present sulcus speculum placed adjacent the sulcus.

An embodiment of the present sulcus speculum is shown in FIG. 3 and includes a speculum 10. The speculum 10 includes a pair of arms 12 and can include a mechanism 14 for spreading the arms apart. At least one of the pair of arms 12 has a portion with a shape adapted for reaching under the eyelid of a patient to the sulcus. The arm portion with that shape will be referred to as the sulcus arm portion 16. In some embodiments the sulcus arm portion 16 can help hold the eyelid open during ophthalmic procedures.

As shown in FIG. 3, the sulcus arm portion 16 can have a hole or holes 18 for receiving fluid from the sulcus or for delivering drugs to the sulcus. (Herein, the term "hole" is intended to be interchangeable with the term "opening".) During eye surgery, water and other fluids accumulate in the sulcus. The water can come from a patient's tear ducts, or can be from the operating equipment. To keep the surgical area relatively free of liquid so that the surgeon can clearly see the working area, suction is applied and fluid from the sulcus flows through the hole or holes 18 in the sulcus arm portion 16, through the length of the sulcus arm portion 16, and into a collection area (not shown) located away from the patient's eye.

Alternatively, the sulcus arm portion 16 can be used to deliver drugs to the sulcus. Pumping drugs through the sulcus arm portion 16 so that the drugs exit the holes or openings 18 and enter the sulcus permits drug delivery.

A pump or suction device (not shown) is connected to or is in communication with the speculum 10 to provide suction or pressure depending on the function performed by the sulcus arm portion 16. Also not shown in the Figures is a collection area for collecting fluid from the sulcus or a source of drugs to be pumped to the sulcus.

If the speculum 10 has a spreading mechanism 14, such as the mechanism 14 in FIG. 1, the sulcus arm portion 16 of the speculum 10 can be positioned by the mechanism 14 to open the eyelid a desired amount, positioning the sulcus arm portion 16 adjacent the sulcus, thereby increasing fluid removal from or drug delivery to the sulcus.

Figure 4:
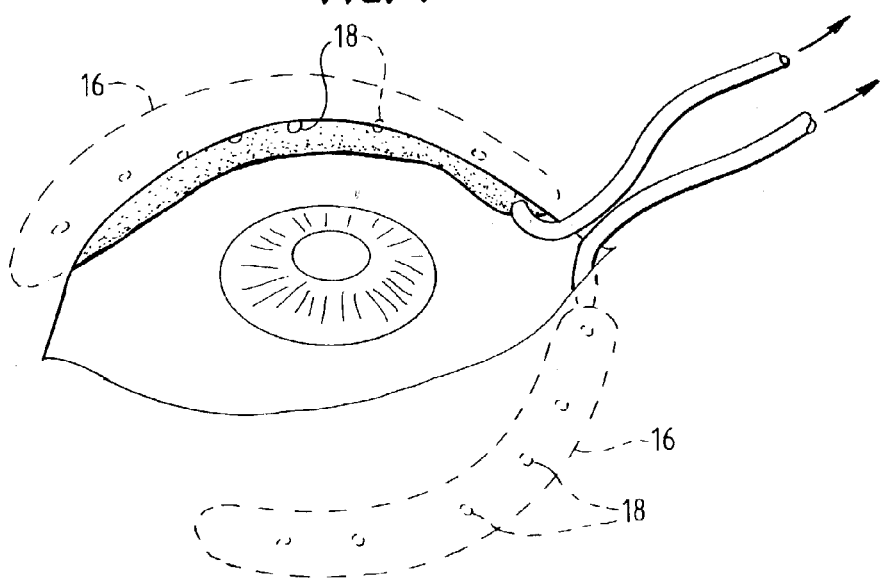
FIG. 4 depicts a portion of one embodiment of the present sulcus speculum placed adjacent the sulcus.

The embodiment of FIG. 3 shows the sulcus arm portions 16 opening the eyelid in conjunction with a wire speculum 10 wrapping around the eyelid margin. FIG. 4 shows the sulcus arm portions 16 holding the eyelid open from the sulcus.

As shown in FIGS. 5 through 10, in some embodiments, at least a portion of the sulcus arm portion 16 can be covered with a porous member 100 made of a porous material such as a sponge or other absorbent or wicking material. In some embodiments, the porous member 100 is shaped to be slipped easily over or onto the sulcus arm portion 16. The porous member 100 can be a disposable member, which can be slipped off of the sulcus arm portion 16 after a single procedure and replaced with a new porous material member 100.

Porous material members 100 can be provided in different lengths so that the system can be used with different size eyes without changing the size of the speculum 10 or the sulcus arm portion 16. If different length porous material members 100 are provided, the longer members will extend farther past the end of the sulcus arm portion 16 of the speculum 10 than will the shorter members.

The porous material member 100 prevents particulate matter suspended in the fluid from clogging the hole or holes 18 of the sulcus arm portion 16. In addition to preventing clogging, the porous material member 100 provides a relatively soft surface for the eyeball to contact, thereby preventing trauma to the eyeball during suction. The porous material member 100 also permits anesthesia or other topical drugs to be applied to the eye. The drugs can be applied by soaking the porous member 100 in the drugs and then positioning the porous member 100 in the sulcus. Because the porous member 100 can be elongated and curved, application of drugs in the sulcus can be relatively uniform.

The porous member 100 and sulcus arm portion 16 can be shaped with a curvature that approximates the curvature of the sulcus. A curvature similar to the curvature of the sulcus increases the contact of the porous material 100 with the fluid of the sulcus to increase the efficiency in removing fluid or delivering drugs through the sulcus arm portion 16.

Figure 5:
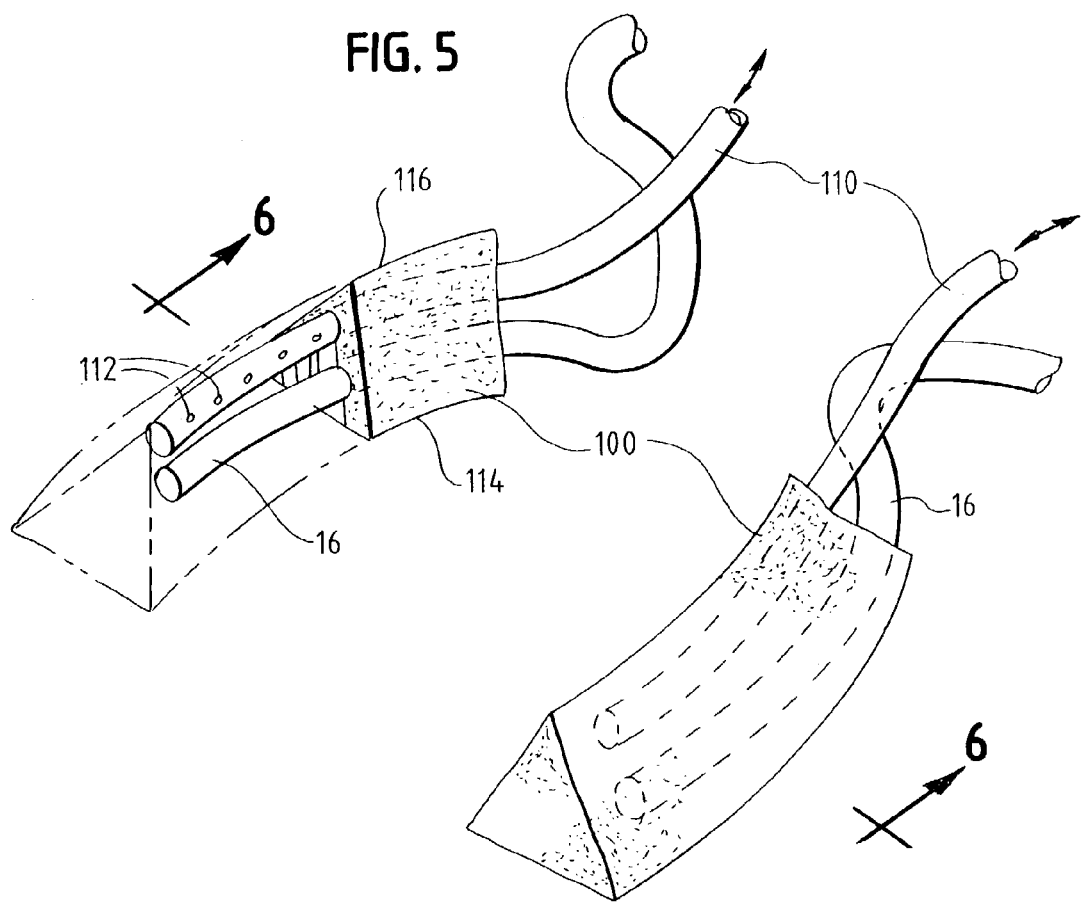
FIG. 5 is a perspective view, partially in section, of a portion of another embodiment of the present sulcus speculum.

As seen in FIG. 5, a porous material member 100, such as a sponge can be used to receive at least a portion of the sulcus arm portion 16 of the speculum arm 12 and at least a portion of an aspiration tube 110. In the embodiment of FIG. 5, the sulcus arm portion 16 of the speculum arm 12 need not have holes 18 because the aspiration tube 110 has at least one hole 112 for receiving fluid from a sulcus of a patient.

Figure 6:
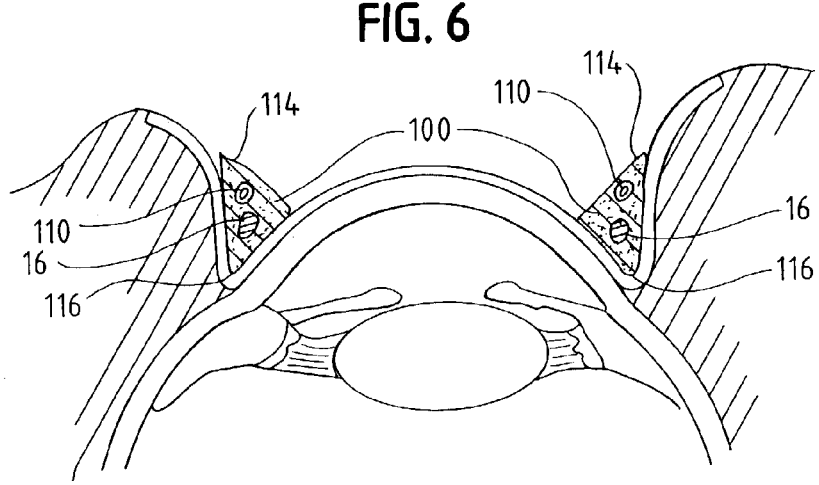
FIG. 6 is a perspective view, partially in section, of a portion of the FIG. 5 embodiment of the present sulcus speculum engaging eyelid margins.

As seen in FIGS. 5 and 6, the porous material 100 can have a wide portion 114 and a relatively narrow portion 116. The wide portion 114 can be positioned nearest the working area of the eye during an ophthalmic procedure, because the wide portion 114 can help keep an eyelid propped open. The narrow portion 116 can be positioned in or adjacent the sulcus to absorb fluid. Fluid from the sulcus enters the hole or holes 112 in the aspiration tube 110 and flows to a collection area (not shown). A pump or other mechanism (not shown) can provide suction in the aspiration tube 110. Alternatively, the aspiration tube 110 can be used to deliver drugs to the sulcus. Pumping drugs through the aspiration tube 110 so that the drugs exit the hole or holes 112 and enter the sulcus permits drug delivery. The aspiration tube 110 can also be used on the sulcus to provide continuous flow of antibiotics or steroids, or to neutralize ph on the eye for lye or acid injuries.

Figure 7:
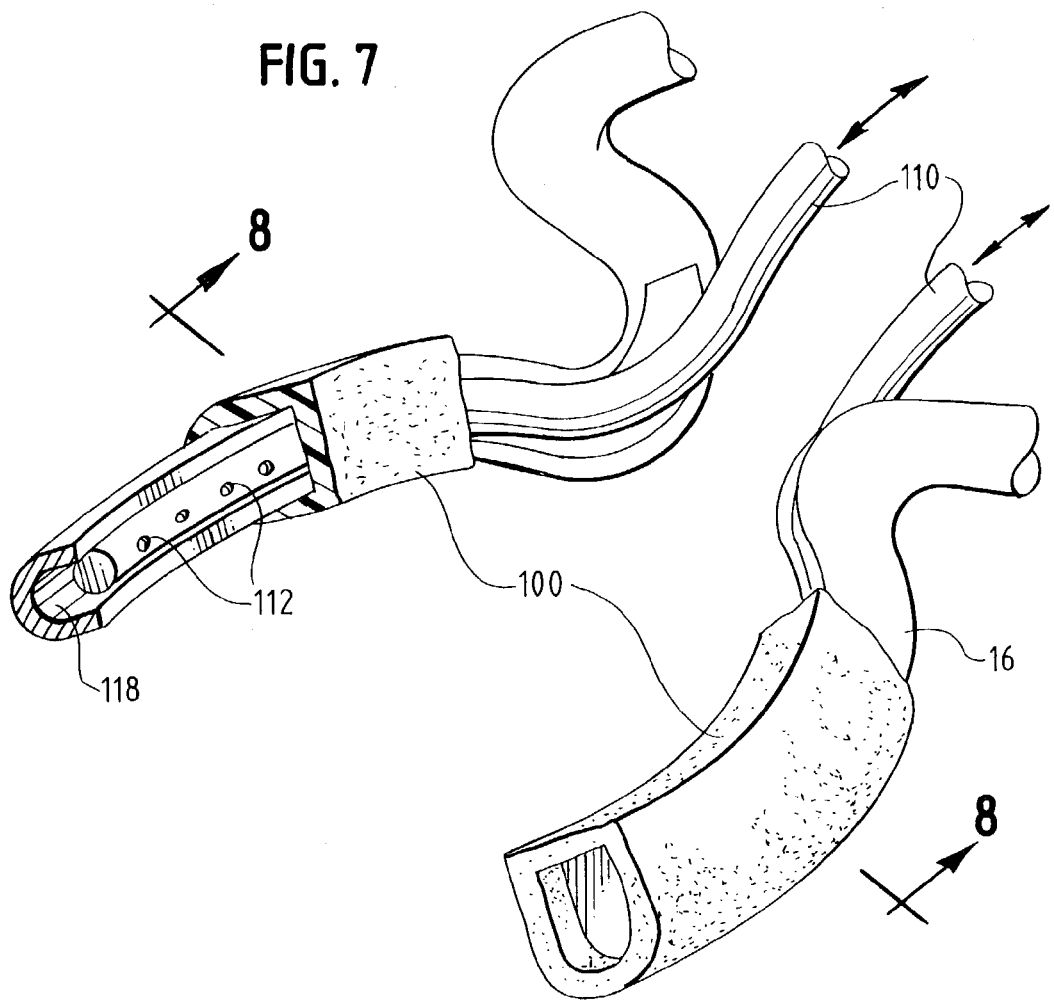
FIG. 7 is a perspective view, partially in section, of a portion of another embodiment of the present sulcus speculum.
Figure 8:
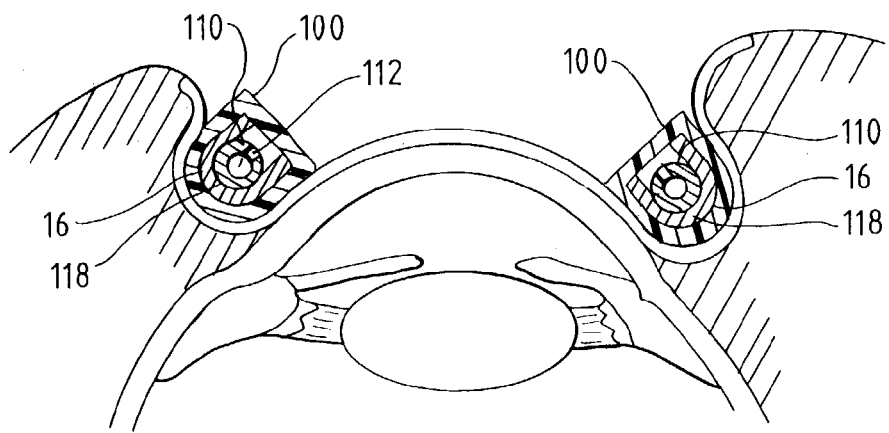
FIG. 8 is a perspective view, partially in section, of a portion of the FIG. 7 embodiment of the present sulcus speculum engaging eyelid margins.
Figure 9:
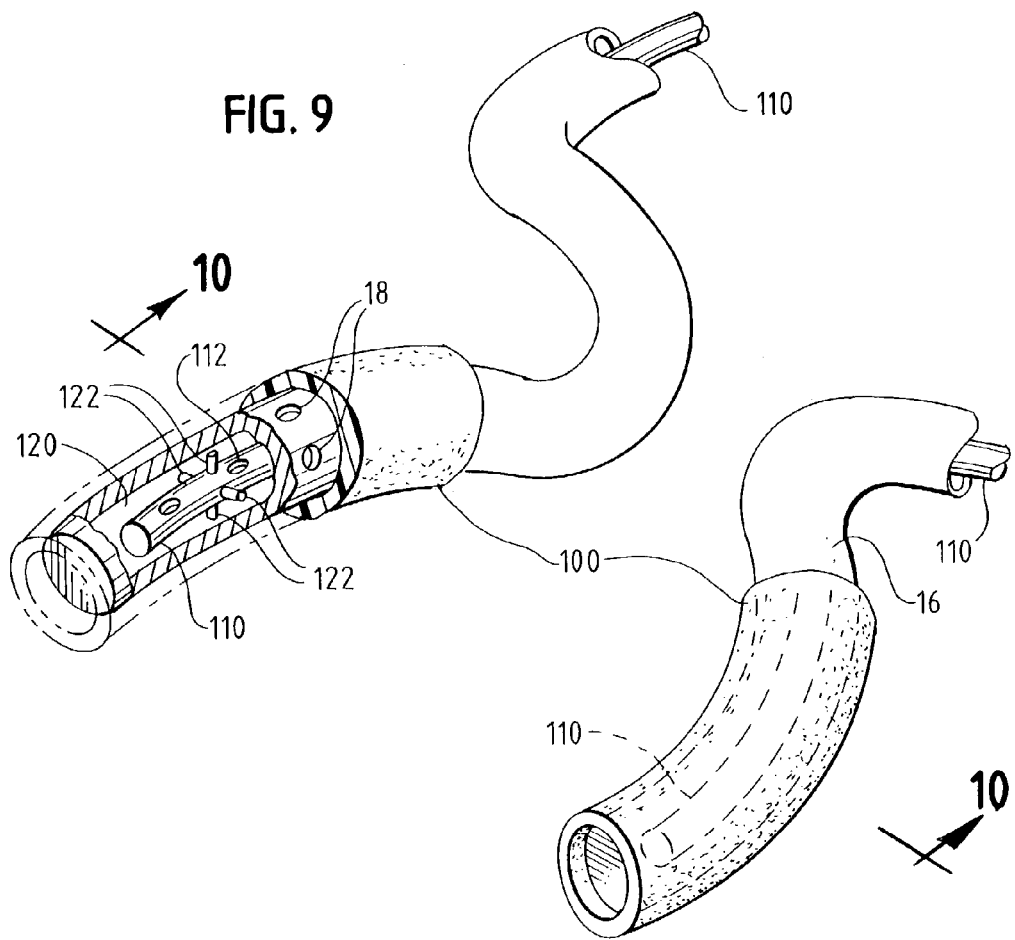
FIG. 9 is a perspective view, partially in section, of a portion of another embodiment of the present sulcus speculum.
Figure 10:
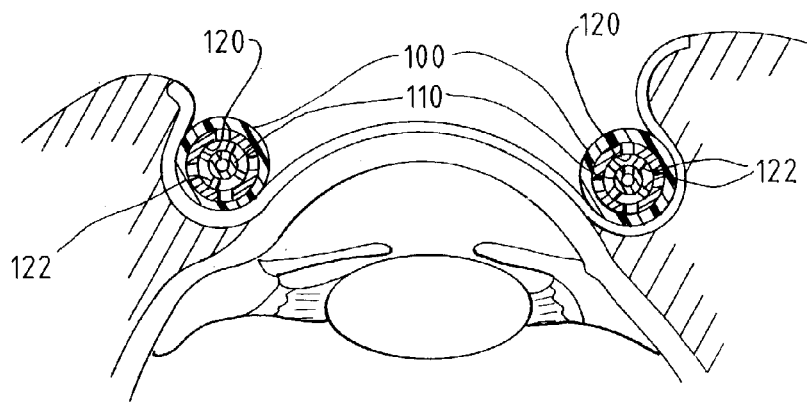
FIG. 10 is a perspective view, partially in section, of a portion of the FIG. 9 embodiment of the present sulcus speculum engaging eyelid margins.

The porous member 100 can have shapes other than the shape shown in FIG. 5. For example, instead of sharp corners and edges or wide portions 114 and narrow portions 116, some or all of the corners and edges can be tapered. The porous member 100 can be oval in cross-section, circular in cross-section, square in cross-section, U-shaped in cross-section, or other suitable shape. FIGS. 7 and 8 illustrate a U-shaped cross-section and FIGS. 9 and 10 illustrate a circular cross-section.

The aspiration tube 110 can be made of a suitable material such as, for example, a plastic material like silicone, so that the aspiration tube can be disposable. Alternatively, the tube can be made of metal, such as titanium, which can be easily sterilized. If the tube is made of plastic, the tube can also have a thin wire extending along the tube length to allow a physician to shape the plastic tube, effectively giving the tube a flexibly adjustable shape.

An embodiment similar to the embodiment of FIG. 5 has a porous member 100 that receives an aspiration tube 110 with holes 112 but does not receive a portion of the speculum 10. A physician can position the porous member 100 adjacent the sulcus by using the speculum arm 12 to push the porous member 100 toward the sulcus even though the speculum arm 12 is not received in the porous member 100. Fluid can be pumped into or suctioned out of the sulcus as described in connection with the embodiment of FIG. 3.

FIGS. 7 and 8 depict an embodiment of a device having a speculum 10 that has at least one arm 12 with a sulcus arm portion 16 defining a trough 118. An aspiration tube 110 is disposed in the trough 118 and has at least one hole 112 for receiving fluid from the sulcus. The fluid enters the hole or holes 112 in the aspiration tube 110 and flows to a collection area (not shown). A pump or other mechanism (not shown) can provide suction in the aspiration tube 110. In use, the convex side of the sulcus arm portion 16 is placed in the sulcus and an interior of the sulcus arm portion 16 (which defines the trough 118) is positioned to face the surgical site. The embodiment of FIGS. 7 and 8 can help prop an eyelid open. As an alternative to removing fluid, the embodiment of FIGS. 7 and 8 can be used to deliver drugs to the sulcus through the hole or holes 112 of the aspiration tube 110 as described for the aspiration tube 110 of FIG. 5.

In some embodiments, a porous member 100 such as a sponge can be disposed around at least a portion of the speculum arm 12. The member 100 can extend around an exterior of the arm 12 and cover at least a portion of the trough 118, as seen in FIGS. 7 and 8. Porous material members 100 can be produced in different lengths so that the fluid removal system can be used with different size eyes without changing the size of the speculum 10. The porous member 100 can provide the same advantages to the embodiment of FIGS. 7 and 8 as discussed above in connection with the embodiment of FIGS. 5 and 6.

In the embodiment of FIGS. 9 and 10, a speculum 10 has at least one arm 12 with a sulcus arm portion 16 defining a passage 120. The sulcus arm portion 16 defining the passage 120 can have a circular cross-section, an oval cross-section or other shape that can define a passage. The sulcus arm portion 16 has at least one hole 18 for receiving fluid from the sulcus. An aspiration tube 110 is disposed in the passage 120 and has at least one hole 112 for receiving fluid that has passed into the passage 120 through the hole or holes 18 in the sulcus arm portion 16 that defines the passage 120. Although shown as coaxial with the sulcus arm portion in FIGS. 9 and 10, the aspiration tube 110 need not be coaxial with the sulcus arm portion 16.

In operation in the embodiment of FIGS. 9 and 10, fluid enters the hole or holes 18 in the sulcus arm portion 16 and then passes through the hole or holes 112 in the aspiration tube 110 and flows to a collection area (not shown). A pump or other mechanism (not shown) can provide suction in the aspiration tube 110. As an alternative to removing fluid, the embodiment of FIGS. 9 and 10 can be used to deliver drugs to the sulcus through the holes 18 of the sulcus arm portion 16. The embodiment of FIGS. 9 and 10 can help prop an eyelid open in addition to or instead of providing aspiration or drug delivery.

In some embodiments, a porous member 100 such as a sponge or other absorbent or wicking material can be disposed around at least a portion of the sulcus arm portion 16 that defines the passage 120, as seen in FIGS. 9 and 10. The porous member 100 can provide the same advantages to the embodiment of FIGS. 9 and 10 as discussed above in connection with the embodiment of FIGS. 5 and 6. Porous material members 100 can be produced in different lengths so that the fluid removal system can be used with different size eyes without changing the size of the speculum. The present sulcus speculum can be used without a porous member 100 to prop an eyelid open.

The device of FIGS. 9 and 10 can include at least one support member 122 to connect the aspiration tube 110 to the interior of the arm 12 for stability.

One or more of the sulcus arm portion 16 embodiments discussed in connection with FIGS. 5 through 10 can be attached or removably attachable to a lid speculum 10, the lid speculum 10 thus having one or more sulcus arm portions 16 when one of the embodiments of FIGS. 5 through 10 is attached to the lid speculum 10. The lid speculum 10 has a loop or loops 20 or a blade or blades for engaging one or both eyelids. Alternatively, a speculum can have a pair of arms 12 including sulcus arm portions 16 and at least one additional arm with a loop 20 or blade for engaging an eyelid.

Because the sulcus arm portion 16 is positioned in or adjacent the sulcus, there can be room for placing a conventional lid speculum on the eyelid margins without interfering with operation of some embodiments of the present sulcus speculum 10. This embodiment is depicted in FIG. 3.

FIG. 3 shows an embodiment in which the sulcus arm portions 16 are each part of a lid speculum 10. The lid speculum 10 has loops 20 for engaging the lid margin. Although the sulcus arm portions 16 can help open eyelids, the loops 20 of the lid speculum 10 ensure that eyelids remains fixed open. Although FIG. 3 depicts a pair of speculum arms 12 each having a sulcus arm portion 16 and a loop 20, embodiments are contemplated in which only one of the pair of arms 12 has a sulcus arm portion 16. Also, embodiments are contemplated similar to the embodiment of FIG. 3 but having a blade or blades rather than loops 20. The sulcus arm portions 16 of FIG. 3 can be one of the embodiments discussed above in connection with FIGS. 5 through 10, such as a sulcus arm portion 16 with holes 18 (FIGS. 3 and 4), a sulcus arm portion 16 and an aspiration tube 110 received in a sponge (FIGS. 5 and 6), an aspiration tube 110 in a trough 118 defined by the sulcus arm portion 16 (FIGS. 7 and 8), and an aspiration tube 110 in a passage 120 defined by the sulcus arm portion 16 (FIGS. 9 and 10).

FIG. 3 shows a speculum 10 having a pair of arms 12, each arm 12 having at least one loop 20 engaging a lid margin. The loops 20 of the speculum 10 ensure that the eyelids remains fixed open. Connected to the speculum arms 12 are sulcus arm portions 16, which are shown to be under the eyelids and adjacent the sulcus. A speculum 10 in accordance with some embodiments of the present sulcus speculum 10 can have a particular sulcus arm portion 16 embodiment for one eyelid but a different type of sulcus arm portion 10 for the other eyelid. In other words, the embodiments discussed in connection with FIGS. 5 through 10 can be paired in combination to form a speculum 10 in accordance with some embodiments of the present sulcus speculum 10.

In some embodiments, the present speculum 10 can have a pair of arms 12, but only a single sulcus arm portion 16. The sulcus arm portion 16 fits under the eyelid and adjacent the sulcus. The sulcus arm portion 16 is attached to a speculum arm 12 having a loop 20 for engaging a lid margin. The speculum arm 12 without a sulcus arm portion 16 has a loop 20 for engaging an eyelid margin. The embodiments described in connection with FIGS. 5 through 10 can be configured so that only a single speculum arm 12 has the sulcus arm portion 16. In embodiments with only a single sulcus arm portion 16, the speculum 10 lacks symmetry and therefore has either a left-handedness or right-handedness.

In some embodiments, the present speculum 10 can have a pair of arms 12 and a sulcus arm portion 16 for each arm 12. The sulcus arm portion 16 could be similar to the embodiment of FIG. 4 except that the speculum arms 12 could each include a loop 20 for engaging the lid margin as shown in FIG. 2. The sulcus arm portions 16 are shown under the eyelids and adjacent the sulcus. The embodiments discussed above in connection with FIGS. 5 through 10 can be employed as sulcus arm portions 16 in connection with the embodiments shown in FIGS. 3 and 4.

Figure 11:
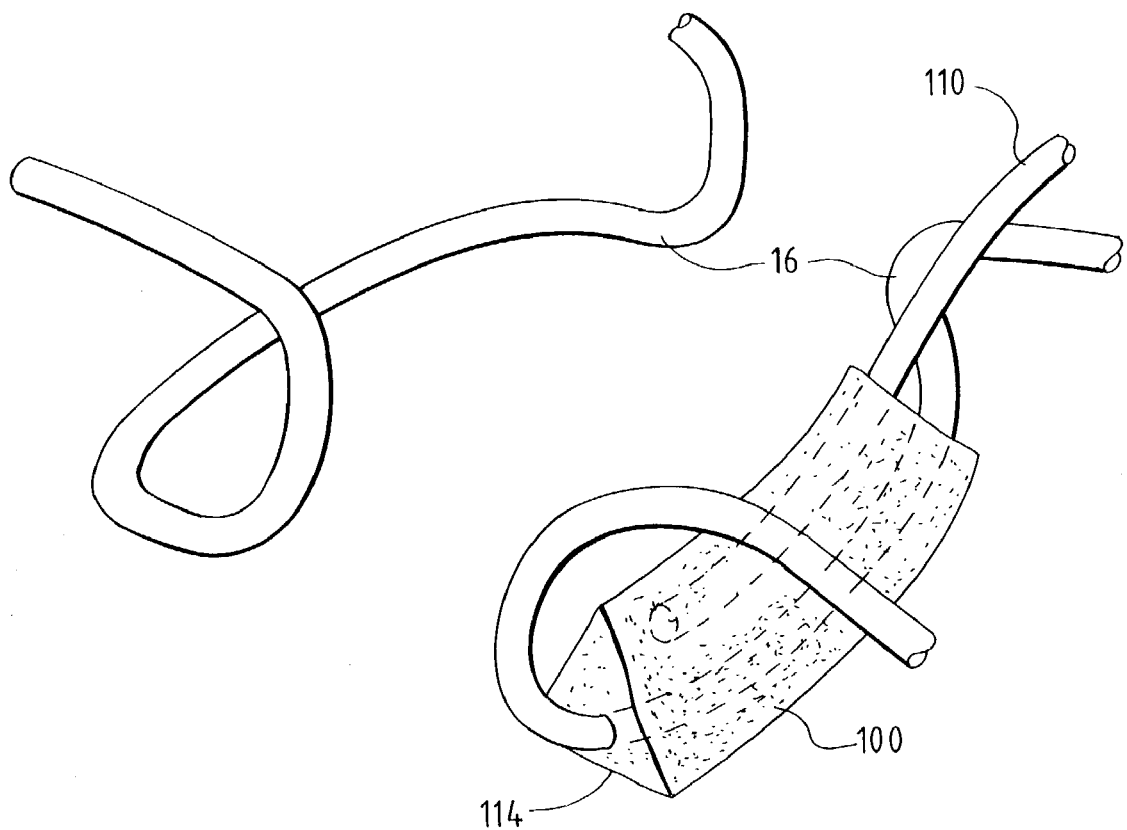
FIG. 11 is a portion of a wire speculum capable of being used as one embodiment of the present sulcus speculum.

As shown in FIG. 11, the sulcus arm portion 16 can also have a hooked section that turns back generally toward the handle of the speculum 10. The hooked section provides extra area to the sulcus arm portion 16, which can improve the ability of the sulcus arm portion 16 to keep the eyelid propped open. Each of the embodiments discussed above in connection with FIGS. 5 through 10 can have a hooked section. The hooked section can be unshaped or other shapes that turn back generally toward the handle of the speculum 10.

In each of the embodiments discussed above having a porous member 100, removal of fluid can be accomplished without using a suction mechanism (for example, a pump). Rather, a porous member 100 can absorb fluid from the sulcus and facilitate movement of the fluid out of the eye by osmotic pressure as the material is draped out and below the level of the eye. Further, a portion of the porous member 100 can extend beyond an end of the sulcus arm portion 16. The portion of the porous member 100 extending beyond the sulcus arm portion 16 end can provide additional wicking and allow a doctor flexibility in positioning the porous member 100 because that portion of the porous member 100 is not restricted by the relatively rigid sulcus arm portion 16 of the speculum 10. Furthermore, because the portion of the porous member 100 extending beyond the sulcus arm portion 16 is attached to the sulcus arm portion 16, the porous member 100 cannot float away. Often, the porous material 100 is a sponge that can float. In conventional wicking techniques, the sponge wicking material tended to float out of the sulcus.

While particular elements, embodiments and applications of the present invention have been shown and described, it will be understood, of course, that the invention is not limited thereto since modifications can be made by those skilled in the art, particularly in light of the foregoing teachings. It is therefore contemplated by the appended claims to cover such modifications as incorporate those features that come within the scope of the invention.

What is claimed is:

1. A device for placement adjacent a sulcus during ophthalmic surgery, the device comprising: (a) a speculum having an arm, wherein a portion of the arm defines a trough; and (b) an aspiration tube having at least one opening formed therein; and (c) at least one support member that connects the aspiration tube to an interior of the portion of the arm defining the trough;

wherein at least a portion of the aspiration tube is disposed in and connected to the trough.

2. The device of claim 1 wherein a cross-section of the trough is v-shaped.

3. The device of claim 1 wherein a cross-section of the trough is u-shaped.

4. The device of claim 1 and comprising a porous member disposed around at least a portion of the portion of the arm defining the trough.

5. The device of claim 4 wherein the porous member is sponge.

6. The device of claim 1 wherein the aspiration tube is curved to follow the curvature of the sulcus.

7. The device of claim 1 and further comprising a wire for engaging a lid margin to separate eyelids of a patient.

\* \* \* \* \*